(12) United States Patent
Yoshida et al.

(10) Patent No.: US 7,368,516 B2
(45) Date of Patent: May 6, 2008

(54) CATALYST FOR TRIMERIZATION OF ETHYLENE AND PROCESS FOR TRIMERIZING ETHYLENE USING THE CATALYST

(75) Inventors: Toru Yoshida, Kuwana (JP); Toshihide Yamamoto, Yokkaichi (JP); Hisanori Okada, Yokkaichi (JP); Hideyuki Murakita, Yokkaichi (JP)

(73) Assignee: Tosoh Corporation, Shinnanyo-shi (JP)

( * ) Notice: Subject to any disclaimer, the term of this patent is extended or adjusted under 35 U.S.C. 154(b) by 327 days.

(21) Appl. No.: 11/090,080

(22) Filed: Mar. 28, 2005

(65) Prior Publication Data

US 2005/0187419 A1    Aug. 25, 2005

Related U.S. Application Data

(63) Continuation of application No. 09/964,587, filed on Sep. 28, 2001, now Pat. No. 6,900,152.

(30) Foreign Application Priority Data

Sep. 29, 2000 (JP) ............................. 2000-302870
Dec. 5, 2000 (JP) ............................. 2000-374700

(51) Int. Cl.
*C08F 110/02* (2006.01)
*C08F 4/22* (2006.01)
*B01J 31/34* (2006.01)
*B01J 31/18* (2006.01)

(52) U.S. Cl. ...................... 526/352; 526/161; 526/104; 502/103; 502/117; 502/123; 502/167

(58) Field of Classification Search ................ 526/352, 526/161, 104; 502/116, 103, 167, 168, 123, 502/117
See application file for complete search history.

(56) References Cited

U.S. PATENT DOCUMENTS

| | | | |
|---|---|---|---|
| 4,870,042 A | 9/1989 | Kohara et al. | |
| 5,237,069 A | 8/1993 | Newman | |
| 5,312,794 A | 5/1994 | Kelsey | |
| 5,519,099 A | 5/1996 | Wang et al. | |
| 5,550,305 A | 8/1996 | Wu | |
| 5,744,677 A | 4/1998 | Wu | |
| 5,753,577 A | 5/1998 | Hamura et al. | |
| 5,770,666 A | 6/1998 | Hamura et al. | |
| 5,811,618 A | 9/1998 | Wu | |
| 5,968,866 A | 10/1999 | Wu | |
| 6,069,110 A | 5/2000 | Klaui et al. | |
| 6,180,552 B1 | 1/2001 | Hlatky | |
| 6,337,297 B1 * | 1/2002 | Mimura et al. | ............. 502/117 |
| 6,362,294 B1 | 3/2002 | Matsunaga et al. | |
| 6,369,253 B1 | 4/2002 | Wilson et al. | |
| 6,501,000 B1 | 12/2002 | Stibrany et al. | |
| 6,593,438 B2 | 7/2003 | Oskam | |
| 6,689,928 B2 | 2/2004 | Stibrany et al. | |
| 2002/0086960 A1 | 7/2002 | Murray | |
| 2002/0103071 A1 | 8/2002 | Oskam | |

* cited by examiner

*Primary Examiner*—Ling-Sui Choi
(74) *Attorney, Agent, or Firm*—Oblon, Spivak, McClelland, Maier & Neustadt, P.C.

(57) ABSTRACT

A catalyst used for trimerization of ethylene into 1-hexene is descrobed, which comprises (i) a specific organometallic complex having a neutral multidentate ligand having a tripod structure, (ii) an alkylaluminoxane, and an optional ingredient selected from:
(iii) a halogenated inorganic compound,
(iv) a specific alkyl group-containing compound,
(v) a combination of a halogenated inorganic compound with a specific alkyl group-containing compound,
(vi) an amine compound and/or an amide compound, and
(vii) a combination of an amine compound and/or an amide compound with a specific alkyl group-containing compound.

8 Claims, No Drawings

CATALYST FOR TRIMERIZATION OF ETHYLENE AND PROCESS FOR TRIMERIZING ETHYLENE USING THE CATALYST

CONTINUING APPLICATION DATA

This application is a Continuation of U.S. application Ser. No. 09/964,587, filed on Sep. 28, 2001, now allowed.

BACKGROUND OF THE INVENTION (1) Field of the Invention

This invention relates to a catalyst for trimerization of ethylene and a process for trimerizing ethylene using the catalyst. More specifically, it relates to a catalyst exhibiting an enhanced activity for trimerization of ethylene to produce 1-hexene, which is used as a comonomer for the production of linear low-density polyethylene (LLDPE), and further to a process for trimerizing ethylene by which 1-hexene can be produced effectively and highly selectively.

(2) Description of the Related Art

It is known to use a chromium compound as a catalyst for trimerization of ethylene to give 1-hexene. For example, a catalyst system comprising a chromium compound, polyhydrocarbylaluminum oxide and a donor ligand is described in Japanese Unexamined Patent Publication No. (hereinafter abbreviated to "JP-A") S62-265237. A catalyst system comprising a chromium compound, a pyrrole-containing compound, an alkyl metal compound and a halide is described in JP-A H6-239920. A catalyst system comprising a chromium compound, an alkyl metal compound, and an acid amide or imide compound is described in JP-A H8-59732. A catalyst comprising (i) a complex of chromium salt with a multidentate ligand selected from phosphine, arsine and stibine, and (ii) aluminoxane is described in JP-A H6-298673. A catalyst comprising (i) a chromium-chlorine complex or alkyl chromium complex having a specific nitrogen ligand and (ii) an aluminum compound is described in JP-A H10-7712. A catalyst comprising (i) a chromium complex having a cyclic polyamine or hydro-tris(pyrazolyl)borate ligand and (ii) an alkyl aluminum compound is described in JP-A H10-231317.

However, these chromium catalysts have problems as explained below.

When the catalyst of JP-A S62-265237 is used for trimerization of ethylene, a large amount of polyethylene is produced in addition to 1-hexene. When the catalyst of JP-A H6-239920 is used, the amount of polyethylene produced can be reduced. However, a pyrrole-containing compound, which is one ingredient of the catalyst, is extremely unstable to air, and readily deteriorated and colored. Thus, a pyrrole-containing compound is troublesome to handle, and a treating process or apparatus for removing a coloring matter from the catalyst or purifying the catalyst is needed.

As for the catalyst of JP-A H8-59732, among the acid amide or imide compounds, which are one ingredient of the catalyst, maleimide is optimum for the catalytic activity for trimerization of ethylene. However, maleimide has problems such that it has a poor solubility in an organic solvent and the catalyst is troublesome to prepare, and further that it is not readily commercially available and is expensive.

The catalyst of JP-A H6-298673 has a problem such that it is difficult to carry out a process for trimerization of ethylene with a good reproducibility. The catalyst of JP-A H10-7712 has a poor activity for trimerization of ethylene. The catalyst of JP-A H10-231317 has problems such that a large amount of polyethylene is undesirably produced, and that the selectivity to 1-hexene among oligomers is low.

SUMMARY OF THE INVENTION

In view of the foregoing, a primary object of the present invention is to provide a catalyst having good handling characteristics and exhibiting an enhanced activity for trimerization of ethylene to produce 1-hexene, which is used as a comonomer for the production of linear low-density polyethylene (LLDPE).

Another object of the present invention is to provide a process for trimerizing ethylene by which 1-hexene can be produced effectively and highly selectively.

In one aspect of the present invention, there is provided a catalyst for trimerization of ethylene which comprises:

(i) an organometallic complex having a neutral multidentate ligand having a tripod structure, represented by the following formula (1):

wherein A is a neutral multidentate ligand having a tripod structure, M is a transition metal atom of group 3 to group 10 of the periodic table, each Q is independently selected from the group consisting of a hydrogen atom, a halogen atom, a straight chain or branched alkyl group having 1 to 10 carbon atoms which may have a substituent, an aryl group having 6 to 10 carbon atoms which may have a substituent, and n is an integer equal to a formal oxidation valence of M, and (ii) an alkylaluminoxane;

said neutral multidentate ligand A in formula (1) being a tridentate ligand represented by the following formula (2) or formula (3):

wherein j, k and m independently represent an integer of 0 to 6, each $D^1$ independently represents a divalent hydrocarbon group which may have a substituent, each $L^1$ independently represents a substituent containing an element of group 14, 15, 16 or 17 of the periodic table, with the proviso that all of the three $L^1$s are not concurrently a substituent containing an element of group 14 or 17, $G^1$ represents a carbon or silicon atom, and $R^1$ represents a hydrogen atom, an alkyl group having 1 to 10 carbon atoms which may have a substituent, or an aryl group having 6 to 10 carbon atoms which may have a substituent;

wherein a, b and c independently represent an integer of 0 to 6; u represents an integer of 0 or 1; each $D^2$ independently represents a divalent hydrocarbon group which may have a substituent; each $L^2$ independently represents a substituent containing an element of group 14, 15, 16 or 17 of the periodic table, with the proviso that all of the three L²s are not concurrently a substituent containing an element an element of group 14 or 17, G² represents a nitrogen or phosphorus atom when u is 0, or a phosphorus atom when u is 1, and R² represents an oxygen or sulfur atom.

In another aspect of the present invention, there is provided a catalyst for trimerization of ethylene which comprises (i) the above-mentioned organometallic complex of formula (1) having a neutral multidentate ligand having a tripod structure, (ii) an alkylaluminoxane, and (iii) a halogenated inorganic compound.

In still another aspect of the present invention, there is provided a catalyst for trimerization of ethylene which comprises (i) the above-mentioned organometallic complex of formula (1) having a neutral multidentate ligand having a tripod structure, (ii) an alkylaluminoxane, (iii) a halogenated inorganic compound, and (iv) an alkyl group-containing compound represented by the following formula (4):

$$R_pEJ_q \quad (4)$$

wherein p and q are numbers satisfying the formulae: $0 < p \leq 3$ and $0 \leq q < 3$, provided that (P+q) is in the range of 1 to 3, E represents an atom, other than a hydrogen atom, of group 1, 2, 3, 11, 12 or 13 of the periodic table, each R independently represents an alkyl group having 1 to 10 carbon atoms, and each J independently represents a hydrogen atom, an alkoxide group having 1 to 10 carbon atoms, an aryloxy group having 6 to 10 carbon atoms, an aryl group having 6 to 10 carbon atoms or a halogen atom.

In a further aspect of the present invention, there is provided a catalyst for trimerization of ethylene which comprises (i) the above-mentioned organometallic complex of formula (1) having a neutral multidentate ligand having a tripod structure, (ii) an alkylaluminoxane, and (iii) the above-mentioned alkyl group-containing compound of formula (4).

In a further aspect of the present invention, there is provided a catalyst for trimerization of ethylene which comprises (i) the above-mentioned organometallic complex of formula (1) having a neutral multidentate ligand having a tripod structure, (ii) an alkylaluminoxane, and (iii) an amine compound and/or an amide compound.

In a further aspect of the present invention, there is provided a catalyst for trimerization of ethylene which comprises (i) the above-mentioned organometallic complex of formula (1) having a neutral multidentate ligand having a tripod structure, (ii) an alkylaluminoxane, (iii) an amine compound and/or an amide compound, and (iv) the above-mentioned alkyl group-containing compound of formula (4).

In a further aspect of the present invention, there is provided a process for trimerizing ethylene, characterized in that ethylene is trimerized in the presence of the above-mentioned catalysts.

DESCRIPTION OF THE PREFERRED EMBODIMENTS

The catalyst of the present invention used for trimerization of ethylene comprises (i) an organometallic complex having a neutral multidentate ligand having a tripod structure, represented by the following formula (1), and (ii) an alkylaluminoxane.

$$AMQ_n \quad (1)$$

wherein A is a neutral multidentate ligand having a tripod structure, M is a transition metal atom of group 3 to group 10 of the periodic table, each Q is independently selected from the group consisting of a hydrogen atom, a halogen atom, a straight chain or branched alkyl group having 1 to 10 carbon atoms which may have a substituent, an aryl group having 6 to 10 carbon atoms which may have a substituent, and n is an integer equal to a formal oxidation valence of M.

The neutral multidentate ligand A in formula (1) is a tridentate ligand represented by the following formula (2) or formula (3):

wherein j, k and m independently represent an integer of 0 to 6, each $D^1$ independently represents a divalent hydrocarbon group which may have a substituent, each $L^1$ independently represents a substituent containing an element of group 14, 15, 16 or 17 of the periodic table, with the proviso that all of the three $L^1$s are not concurrently a substituent containing an element of group 14 or 17, $G^1$ represents a carbon or silicon atom, and $R^1$ represents a hydrogen atom, an alkyl group having 1 to 10 carbon atoms which may have a substituent, or an aryl group having 6 to 10 carbon atoms which may have a substituent;

wherein a, b and c independently represent an integer of 0 to 6; u represents an integer of 0 or 1; each $D^2$ independently represents a divalent hydrocarbon group which may have a substituent; each $L^2$ independently represents a substituent containing an element of group 14, 15, 16 or 17 of the periodic table, with the proviso that all of the three $L^2$s are not concurrently a substituent containing an element an element of group 14 or 17, $G^2$ represents a nitrogen or phosphorus atom when u is 0, or a phosphorus atom when u is 1, and $R^2$ represents an oxygen or sulfur atom.

The divalent hydrocarbon groups $D^1$ in formula (2) and $D^2$ in formula (3) are not particularly limited, and include, for example, alkylene, cycloalkylene, phenylene, tolylene and xylylene groups. $D^1$ and $D^2$ may have a substituent, for example, an alkyl group such as methyl or ethyl, and an alkoxy group such as methoxy and ethoxy.

The substituents $L^1$ in formula (2) and $L^2$ in formula (3), which contain an element of group 14, 15, 16 or 17 of the periodic table, are not particularly limited. As specific examples of the substituents $L^1$ and $L^2$, there can be mentioned alkoxy groups such as methoxy, ethoxy, propoxy and butoxy; aryloxy groups such as phenoxy and 2,6-dimethylphenoxy; alkylthio groups such as methylthio, ethylthio, propylthio and butylthio; arylthio groups such as phenylthio and tolylthio; dialkylamino groups such as dimethylamino, diethylamino and bis(trimethylsilyl)-amino; diarylamino groups such as diphenylamino; alkylarylamino groups such as methylphenylamino; dialkylphosphino groups such as dimethylphosphino and diethylphosphino; diarylphosphino groups such as diphenylphosphino and ditolylphosphino; and alkylarylphosphino groups such as methylphenylphosphino.

The substituents $L^1$ and $L^2$ further include heterocyclic groups containing an element of group 14, 15, 16 or 17 of the periodic table, such as furyl, benzofuryl, thienyl, benzothienyl, pyrazolyl, triazolyl, tetrazolyl, pyridyl, imidazolyl, benzoimidazolyl, indazolyl, quinolyl, isoquinolyl, oxazolyl and thiazol. These heterocyclic groups may have a substituent on the ring thereof, such as, for example, methyl, ethyl, propyl, butyl, octyl and phenyl.

$R^1$ in formula (2) is not particularly limited, and include, for example, a hydrogen atom, alkyl groups having 1 to 10 carbon atoms, which may have a substituent, such as methyl, ethyl, propyl, butyl, benzyl, hydroxymethyl, cyanoethyl, allyl and trifluoropropyl, and aryl groups having 6 to 10 carbon atoms, which may have a substituent, such as phenyl, p-methylphenyl and p-chlorophenyl.

The neutral tridentate ligand having a tripod structure, represented by formula (2) or (3), which has a substituent containing an element of group 14, 15, 16 or 17 of the periodic table, is not particularly limited. As specific examples of the neutral tridentate ligand, there can be mentioned oxygen-containing tridentate ligands such as tris(methoxymethyl)methane, 1,1,1-tris(methoxymethyl) ethane, 1,1,1-tris(methoxymethyl)propane, 1,1,1-tris(methoxymethyl)butane, 1,1,1-tris(ethoxymethyl)ethane, 1,1,1-tris(propoxymethyl)ethane, 1,1,1-tris(butoxymethyl)ethane and 1,1,1-tris(phenoxymethyl)ethane; sulfur-containing tridentate ligands such as 1,1,1-tris(methylthiomethyl)ethane, 1,1,1-tris(butylthiomethyl)ethane and 1,1,1-tris(phenylthiomethyl)ethane; nitrogen-containing tridentate ligands such as 1,1,1-tris(dimethylaminomethyl)ethane and 1,1,1-tris (diphenylaminomethyl)ethane; and phosphorus-containing tridentate ligands such as 1,1,1-tris(diphenylphosphinomethyl)ethane 1,1,1-tris(dimethylphosphinomethyl)ethane and 1,1,1-tris(diethylphosphinomethyl)ethane.

As specific examples of the neutral tridentate ligand having a tripod structure, represented by formula (2) or (3), which has a heterocyclic substituent containing an element of group 14, 15, 16 or 17 of the periodic table, there can be mentioned oxygen-containing tridentate ligands such as trifurylmethane, tris(5-methyl-2-furyl)methane, tris(5-ethyl-2-furyl)methane, tris(5-butyl-2-furyl)methane, 1,1,1-trifurylethane, trifurylamine, trifurylphosphine and trifurylphosphine oxide; sulfur-containing tridentate ligands such as tris(thienyl)methane; and nitrogen-containing tridentate ligands such as tris(pyrazolyl)methane, tris(3,5-dimethyl-1-pyrazolyl)methane, tris(3,5-diisopropyl-1-pyrazolyl)methane, tris(3,5-diphenyl-1-pyrazolyl)methane, 1,1,1-tris(3,5-dimethyl-1-pyrazolyl)ethane, 1,1,1-tris(3,5-dimethyl-1-pyrazolyl)propane, 1,1,1-tris(3,5-dimethyl-1-pyrazolyl) butane, tris(2-pyridyl)methane, tris(6-methyl-2-pyridyl) methane, tris(2-pyridyl)amine, tris(2-pyridyl)phosphine, tris (2-pyridyl)phosphine oxide, tris(2-pyridyl) hydroxymethane, tris(1-imidazolyl)methane, tris(3,5-dimethyl-1-pyrazolyl)methane, tris(3,5-diethyl-1-pyrazolyl) ethane, tris(3,4,5-trimethyl-1-pyrazolyl)methane, tris(3,5-dimethyl-4-n-butyl-1-pyrazolyl)methane, tris(3-phenyl-5-methyl-1-pyrazolyl)methane, tris(3-(4-tolyl)-5-methyl-1-pyrazolyl)methane, tris(3-(4-anisyl)-5-methyl-1-pyrazolyl) methane, tris(3-(2-pyridyl)-5-methyl-1-pyrazolyl)methane, tris(3-(3-pyridyl)-5-methyl-1-pyrazolyl)methane, tris(3-(4-pyridyl)-5-methyl-1-pyrazolyl)methane, tris(3-phenyl-1-pyrazolyl)methane, 1-methyl-tris(3-phenyl-1-pyrazolyl) methane, methyl-tris(3-ethyl-1-pyrazolyl)methane, methyl-tris(3-phenyl-1-pyrazolyl)methane, methyl-tris(3,5-dimethyl-1-pyrazolyl)methane, tris(3-(4-tolyl)-1-pyrazolyl) methane, tris(3-(4-anisyl)-1-pyrazolyl)methane, tris(3-propyl-1-pyrazolyl)methane, tris(3-ethyl-1-pyrazolyl) methane, tris(3-methyl-1-pyrazolyl)methane and tris(3-t-butyl-1-pyrazolyl)methane.

A halogen atom in Q of formula (1) is not particularly limited, and includes, for example, fluorine, chlorine, bromine and iodine atoms. A straight chain or branched alkyl group having 1 to 10 carbon atoms in Q of formula (1) is not particularly limited, and may have a substituent. Such alkyl group includes, for example, methyl, ethyl, propyl, butyl, cyclohexyl and benzyl groups. An aryl group having 6 to 10 carbon atoms in Q of formula (1) is also not particularly limited, and may have a substiruent. Such aryl group includes, for example, a phenyl group.

The above-mentioned organometallic complex having a neutral multidentate ligand having a tripod structure is not particularly limited, provided that the complex has a composition satisfying formula (1). A preferable example of the organometallic complex is a chromium complex of formula (1) wherein M is a chromium atom of group 6 of the periodic table. As specific examples of the chromium complex of formula (1), there can be mentioned tris(methoxymethyl) methanechromium trichloride (III), tris(methoxymethyl) methanechromium(benzyl) dichloride (III), 1,1,1-tris(methoxymethyl)ethanechromium trichloride (III), 1,1,1-tris (ethoxymethyl)ethanechromium trichloride (III), 1,1,1-tris (butoxymethyl)ethanechromium trichloride (III), 1,1,1-tris (phenoxymethyl)ethanechromium trichloride (III), trifurylmethanechromium trichloride (III), 1,1,1-tris(methylthiomethyl)ethanechromium trichloride (III), 1,1,1-tris (dimethylaminomethyl)ethanechromium trichloride (III), tris(pyrazolyl)methanechromium trichloride (III), tris(3,5-dimethyl-1-pyrazolyl)methanechromium trichloride (III), tris(3,5-diethyl-1-pyrazolyl)methanechromium trichloride (III), tris(3,5-dimethyl-1-pyrazolyl)methyl-methanechromium trichloride (III), tris(3-phenyl-5-methyl-1-pyrazolyl) methanechromium trichloride (III), tris(3-(2-pyridyl)-5-methyl-1-pyrazolyl)methanechromium trichloride (III), tris(3-(3-pyridyl)-5-methyl-1-pyrazolyl)methanechromium trichloride (III), tris(3-(4-pyridyl)-5-methyl-1-pyrazolyl) methanechromium trichloride (III), tris(3-phenyl-1-pyrazolyl)methanechromium trichloride (III), tris(3-(3-tolyl)-5-methyl-1-pyrazolyl)methanechromium trichloride (III), tris (3-(3-anisyl)-5-methyl-1-pyrazolyl)methanechromium trichloride (III), tris(3,5-dimethyl-1-pyrazolyl)methanechromium(hydride) dichloride (III), tris(3,5-dimethyl-1-pyrazolyl)methanechromium(benzyl) dichloride (III), tris(3,5-dimethyl-1-pyrazolyl)methanechromium(ethyl) dichloride (III), tris(3,5-dimethyl-1-pyrazolyl)methanechromium tribenzyl (III), 1,1,1-tris(3,5-dimethyl-1-pyrazolyl) ethanechromium trichloride (III), tris(3,5-diisopropyl-1-pyrazolyl)methanechromium trichloride (III), tris(3-isopropyl-1-pyrazolyl)methanechromium trichloride (III), tris(3-ethyl-1-pyrazolyl)methanechromium trichloride (III), tris(3, 5-diphenyl-1-pyrazolyl)methanechromium trichloride (III), tris(2-pyridyl)methanechromium trichloride (III), tris(6-methyl-2-pyridyl)methanechromium trichloride (III), tris(2-pyridyl)aminechromium trichloride (III), tris(1-imidazolyl) methanechromium trichloride (III), 1,1,1-tris (dimethylphosphinomethyl)ethanechromium trichloride (III), 1,1,1-tris(diphenylphosphinomethyl)ethanechromium trichloride (III) and 1,1,1-tris(diethylphosphinomethyl) ethanechromium trichloride (III).

The above-mentioned organometallic complex having a neutral multidentate ligand having a tripod structure is not particularly limited, provided that the complex has a composition satisfying formula (1).

The organometallic complex of formula (1) wherein M is a transition metal atom, other than chromium atom, of group 3 to group 10 of the periodic table is not particularly limited, and includes, for example, organometallic complexes of formula (1) wherein M is scandium, titanium, zirconium, hafnium, vanadium, molybdenum, tungsten, manganese, iron, ruthenium, cobalt, rhodium, iridium, nickel, vanadium and platinum.

In view of the catalytic activity, among the neutral multidentate ligands having a tripod structure of formulae (2) and (3), a nitrogen-containing tridentate ligand having a heterocyclic group is preferable. As specific examples of the nitrogen-containing tridentate ligand having a heterocyclic group, there can be mentioned tris(3-(4-tolyl)-1-pyrazolyl)methane, tris(3-phenyl-1-pyrazolyl)methane, tris(3,5-dimethyl-1-pyrazolyl)methane, tris(3-phenyl-5-methyl-1-pyrazolyl)methane, tris(3-(2-pyridyl)-5-methyl-1-pyrazolyl)methane, tris(3-(3-pyridyl)-5-methyl-1-pyrazolyl)methane and tris(3-(4-pyridyl)-5-methyl-1-pyrazolyl)methane. As B of formula (1), a halogen atom is preferably used.

As specific examples of preferable organometallic complexes having a neutral tridentate ligand having a heterocyclic group, there can be mentioned (3-(4-tolyl)-1-pyrazolyl)methanechromium trichloride (III), tris(3-phenyl-1-pyrazolyl)methanechromium trichloride (III), tris(3-phenyl-1-pyrazolyl)methanetitanium trichloride (III), tris(3-phenyl-1-pyrazolyl)methanescandium trichloride (III), tris(3-phenyl-1-pyrazolyl)methanemolybdenum trichloride (III), tris(3-phenyl-1-pyrazolyl)methanetungsten trichloride (III), tris(3-phenyl-1-pyrazolyl)methaneiron trichloride (III), tris(3-phenyl-1-pyrazolyl)methaneiron dichloride (II), tris(3,5-dimethyl-1-pyrazolyl)methanechromium trichloride (III), tris(3,5-dimethyl-1-pyrazolyl)methanemolybdenum trichloride (III), tris(3,5-dimethyl-1-pyrazolyl)methanetungsten trichloride (III), tris(3,5-dimethyl-1-pyrazolyl)methanetitanium trichloride (III), tris(3,5-dimethyl-1-pyrazolyl)methanescandium trichloride (III), tris(3,5-dimethyl-1-pyrazolyl)methaneiron dichloride (II), tris(3,5-dimethyl-1-pyrazolyl)methaneiron trichloride (III), tris(3,5-dimethyl-1-pyrazolyl)methanenickel dichloride (II), tris(3,5-dimethyl-1-pyrazolyl)methanepalladium dichloride (II), tris(3,5-dimethyl-1-pyrazolyl)methaneplatinum dichloride (II), tris(3-phenyl-5-methyl-1-pyrazolyl)methanechromium trichloride (III), tris(3-phenyl-5-methyl-1-pyrazolyl)methanescandium trichloride (III), tris(3-phenyl-5-methyl-1-pyrazolyl)methanetitanium trichloride (III), tris(3-phenyl-5-methyl-1-pyrazolyl)methaneiron trichloride (III), tris(3-phenyl-5-methyl-1-pyrazolyl)methaneiron dichloride (II), tris(3-phenyl-5-methyl-1-pyrazolyl)methanenickel dichloride (II), tris(3-phenyl-5-methyl-1-pyrazolyl)methanenickel trichloride (III), tris(3-(2-pyridyl)-5-methyl-1-pyrazolyl)methanechromium trichloride (III), tris(3-(3-pyridyl)-5-methyl-1-pyrazolyl)methanechromium trichloride (III) and tris(3-(4-pyridyl)-5-methyl-1-pyrazolyl)methanechromium trichloride (III).

A process of synthesizing an organometallic complex of the present invention is not particularly limited. The organometallic complex can be easily synthesized from the above-mentioned neutral multidentate ligand having a tripod structure and a transition metal compound by a known organometallic synthesis process, for example, described in Inorg. Chem., 25, 1080 (1986). The transition metal compound used for synthesis of the organometallic complex is not particularly limited, and includes, for example, tris(tetrahydrofuran)scandium chloride (III), tris(tetrahydrofuran)titanium chloride (III), tris(tetrahydrofuran)molybdenum chloride (III), tris(tetrahydrofuran)tungsten chloride (III), chromium chloride (II), chromium bromide (II), chromium bromide (III), chromium iodide (III), chromium iodide (II), chromium fluoride (III), chromium fluoride (II), tris(tetrahydrofuran)chromium trichloride (III), tris(1,4-dioxane)chromium trichloride (III), tris(diethyl ether)chromium trichloride (III), tris(pyridine)chromium trichloride (III), tris(acetonitrile)chromium trichloride (III), iron chloride (II), iron chloride (III), nickel chloride (II), nickel chloride (III), palladium chloride (II) and platinum chloride (II).

The concentration of a transition metal in a reaction solution for synthesis of the organometallic complex is not particularly limited. The solvent used for synthesis of the organometallic complex is not particularly limited, and organic solvents are preferably used. As specific examples of the organic solvent, there can be mentioned aliphatic hydrocarbons such as pentane, hexane, heptane, octane, nonane, decane, cyclohexane and decalin; aromatic hydrocarbons such as benzene, toluene, xylene, cumene and trimethylbenzene; ethers such as diethyl ether and tetrahydrofuran; and halogenated hydrocarbons such as methylene chloride, chloroform and carbon tetrachloride. These organic solvents may be used either alone or as a mixture of at least two thereof.

Synthesis of the organometallic complex is usually carried out at a temperature in the range of −80° C. to the boiling point of solvent used, preferably in the range of 20 to 200° C. A temperature higher than the boiling point of solvent may also be employed provided that the reaction is conducted under pressure. The reaction time is not particularly limited and is usually in the range of 1 minute to 48 hours, preferably 5 minutes to 24 hours. The operation for the organometallic complex synthesis is preferably carried out under conditions such that the reactants are not in contact with air and moisture. The raw materials used are preferably preliminarily dried.

Another process for synthesizing the organometallic complex having a neutral multidentate ligand having a tripod structure can be employed wherein an organometallic halogen complex having a neutral multidentate ligand having a tripod structure, synthesized by the above-mentioned process, is allowed to react with, for example, an alkylaluminoxane or a metal hydride in a solvent.

The thus-produced organometallic complex having a neutral multidentate ligand having a tripod structure usually precipitates, and therefore, can be separated from the solvent by filtration. If desired, the separated organometallic complex is washed with the same solvent, and then dried. If the produced organometallic complex does not precipitate, it can be precipitated by removing the solvent by distillation, adding a poor solvent, or cooling the reaction product mixture.

Among the organometallic complexes having a neutral multidentate ligand having a tripod structure, those in which the multidentate ligand is facially coordinated are preferable because production of side-reaction products such as polyethylene is minimized. By the term "facially coordinated" used herein, we mean that the neutral multidentate ligands occupy the three coordinate sites to form an isomer of six-coordinate octahedral complex (Kagaxu-Sensho: Organic Metal Chemistry, Fundamental and Application, p 143, published by Shoukabou, Japan). That is, three multidentate ligands are coordinated in a configuration such that the three sites take a cis-form to each other in the six-coordinate octahedral complex.

The catalyst of the invention comprises an alkylaluminoxane as another indispensable ingredient, in addition to the organometallic complex of formula (1). The alkylaluminoxane is an aluminum oxy compound having an aluminum-oxygen bond and is not particularly limited, but those which are represented by the following formulae (5) and (6) are preferable.

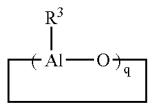

(5)

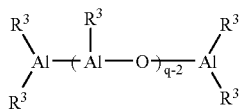

(6)

wherein each $R^3$ independently represents a hydrogen atom or a hydrocarbon group having 1 to 20 carbon atoms, and q is an integer of 2 to 60. As specific examples of $R^3$ in formulae (5) and (6), there can be mentioned a hydrogen atom, and methyl, ethyl, propyl, n-butyl, isobutyl and tert-butyl. The amount of the alkylaluminoxane is usually in the range of 0.1 to 10,000 equivalent, preferably 0.5 to 8,000 equivalent and more preferably 1 to 5,000 equivalent, as aluminum, per mol of the organometallic complex of formula (1).

In one aspect, the catalyst of the present invention comprises an alkyl group-containing compound, in addition to the organometallic complex of formula (1) having a neutral multidentate ligand having a tripod structure and an alkylalumioxane. The alkyl group-containing compound is not particularly limited, but those which are represented by the following formula (4) are preferable:

$$R_p E J_q \quad (4)$$

wherein p and q are numbers satisfying the formulae: $0<p\leq 3$ and $0\leq q<3$, provided that (P+q) is in the range of 1 to 3, E represents an atom, other than a hydrogen atom, of group 1, 2, 3, 11, 12 or 13 of the periodic table, each R independently represents an alkyl group having 1 to 10 carbon atoms, and each J independently represents a hydrogen atom, an alkoxide group having 1 to 10 carbon atoms, an aryloxy group having 6 to 10 carbon atoms, an aryl group having 6 to 10 carbon atoms or a halogen atom.

As examples of the alkyl group R having 1 to 10 carbon atoms in formula (4), there can be mentioned methyl, ethyl, propyl, butyl, cyclohexyl and octyl groups. As specific examples of J in formula (4), there can be mentioned a hydrogen atom, alkoxide groups having 1 to 10 carbon atoms such as methoxide, ethoxide and butoxide groups, aryloxy groups having 6 to 10 carbon atoms such as a phenoxide group, aryl groups having 6 to 10 carbon atoms such as phenyl group, and halogen atoms such as fluorine, chlorine, bromine and iodine.

In formula (4), when E is aluminum, each of p and q is 1.5, the alkyl group-containing compound is represented by the formula $AlR_{1.5}J_{1.5}$. Theoretically this compound does not exist, but, it is popularly called as a sesqui-compound of $Al_2R_3J_3$ and can be used as an example of the alkyl group-containing compound in the present invention.

As specific examples of the alkyl group-containing compound, there can be mentioned methyllithium, ethyllithium, propyllithium, n-butyllithium, sec-butyllithium, tert-butyllithium, diethylmagnesium, ethylbutylmagnesium, ethylchloromagnesium, ethylbromomagnesium, dimethylzinc, diethylzinc, dibutylzinc, trimethylborane, triethylborane, trimethylaluminum, triethylaluminum, tri-n-butylaluminum, triisobutylaluminum, tri-n-hexylaluminum, tri-n-octylaluminum, tricyclohexylaluminum, dimethylethylaluminum, diethylaluminum hydride, diisobutylaluminum hydride, diethylaluminum ethoxide, diethylaluminum phenoxide, dicyclohexylphenylaluminum, ethylaluminum ethoxychloride, diethylaluminum chloride, diethylaluminum bromide, diisobutylaluminum chloride, dicyclohexylaluminum chloride, methylaluminum sesquichloride, ethylaluminum sesquichloride, butylaluminum sesquichloride, ethylaluminum dichloride and isobutylaluminum dichloride.

Of these, trialkylaluminum compounds are preferable in view of commercial availability and catalytic activity. Trimethylaluminum, trethylaluminum, triisobutylaluminum, tri-n-butylaluminum, tri-n-hexylaluminum and tri-n-octylaluminum are mentioned as specific examples of the trialkylaluminum compounds. These alkyl group-containing compounds may be used either alone or as a mixture of at least two thereof.

The amount of the alkyl group-containing compound is usually in the range of 0.1 to 10,000 equivalent, preferably 3 to 3,000 equivalent and more preferably 5 to 2,000 equivalent, per mol of the organometallic complex of formula (1).

In another aspect, the catalyst of the present invention comprises a halogenated inorganic compound, in addition to the organometallic complex of formula (1) having a neutral multidentate ligand having a tripod structure and an alkylalumioxane. The halogenated inorganic compound is not particularly limited, but those which are represented by the following formula (7) are preferable.

$$ZX_h \quad (7)$$

In formula (7), Z is an atom of group 1, 2, 13, 14 or 15 of the periodic table, X represents a halogen atom, and h denoting a number of X is a natural number equal to the formal oxidation valence of Z.

As specific examples of the halogenated inorganic compounds, there can be mentioned hydrogen fluoride, hydrogen chloride, hydrogen bromide, hydrogen iodide, sodium fluoride, sodium chloride, sodium bromide, potassium chloride, magnesium dichloride, boron trifluoride, boron trichloride, thallium trichloride, indium trichloride, gallium trichloride, germanium tetraiodide, germanium tetrachloride, germanium tetrabromide, silicon tetrachloride, silicon tetraiodide, silicon tetrabromide, silicon tetrafluoride, lead tetrachloride, lead tetrafluoride, aluminum trichloride, tin tetrachloride, phosphorus trichloride, phosphorus pentachloride, phosphorus trifluoride, phosphorus tribromide, phosphorus triiodide, antimony trichloride, arsenic pentachloride, antimony pentachloride and bismuth pentachloride. These halogenated inorganic compounds may be used either alone or in combination. The amount of the halogenated inorganic compound is usually in the range of 0.0000001 to 1,000 equivalent, preferably 0.000001 to 500 equivalent and more preferably 0.00001 to 100 equivalent, per mol of the organometallic complex of formula (1).

In still another aspect, the catalyst of the present invention comprises at least one compound selected from amine compound and amide compounds, in addition to the organometallic complex of formula (1) having a neutral multidentate ligand having a tripod structure and an alkylalumioxane. The amine compounds and amide compounds are not particularly limited, but those which have at least one nitrogen atom having three substituents other than hydrogen, and have 3 to 30 carbon atoms are preferable.

As specific examples of the amine compound and the amide compound, there can be mentioned trimethylamine, triethylamine, 1,4-diazabicyclo[2.2.2]octane (DABCO), N-methylindole, N-ethylindole, N-methylmaleimide, N-ethylmaleimide, N-n-propylmaleimide, N-isopropylmaleimide, N-cyclohexylmaleimide, N-phenylmaleimide, N-prenylmaleimide, N-tert-butylmaleimide, 2,6-dimethylpyridine, N-methylaziridine, 4-(N,N-dimethylamino)pyridine (DMAP), 1,8-bis(N,N-dimethylamino)naphthalene (Proton Sponge), N-methylpyrrole, 3,5-dimethyl-N-methylpyrrole, 1,5-diazabicyclo[4.3.0]nonene-5 (DBN), 1,8-diazabicyclo[5.4.0]undecene-7 (DBU), N-phenylpyrrole, N-ethylpyrrole, 5,10,15,20-tetraphenyl-21H,23H-porphine, 21H,23H-porphine, 2,3,7,8,12,13,17,18-octaethyl-21H,23H-porphine and 29H,31H-phthalocyanine. Of these, the above-mentioned maleimides, pyridines and amines having a bridgehead structure are preferable. These amine compounds and amide compounds may be used either alone or as a mixture of at least two thereof.

In view of catalytic activity, the amount of the amine compound and/or the amide compound is usually in the range of 0.1 to 10,000 equivalent, preferably 1 to 5,000 equivalent and more preferably 3 to 100 equivalent, per mol of the organometallic complex of formula (1).

The catalyst of the invention for trimerization of ethylene, which includes (a) a catalyst comprising (i) an orgamnometallic complex of formula (1) and (ii) an alkylaluminoxane; (b) a catalyst comprising (i) an orgamnometallic complex of formula (1), (i) an alkylaluminoxane and (iii) a halogenated inorganic compound; (c) a catalyst comprising (i) an orgamnometallic complex of formula (1), (ii) an alkylaluminoxane, (iv) a halogenated inorganic compound and (iv) an alkyl group-containing compound; (d) a catalyst comprising (i) an orgamnometallic complex of formula (1), (ii) an alkylaluminoxane and (iv) an alkyl group-containing compound; (e) a catalyst comprising (i) an orgamnometallic complex of formula (1), (ii) an alkylaluminoxane and (v) an amine compound and/or an amide compound; and (f) a catalyst comprising (i) an orgamnometallic complex of formula (1), (ii) an alkylaluminoxane, (v) an amine compound and/or an amide compound and (iv) an alkyl group-containing compound, is prepared by placing the organometallic complex of formula (1) (i) into contact with an alkylaminoalumoxane (ii) and other ingredients (iii), (iv) and/or (v) in a solvent in the presence or absence of ethylene. The procedure for contacting these ingredients with each other is not particularly limited.

The concentration of the organometallic complex of formula (1) in the solvent is not particularly limited, but is usually in the range of 0.001 micro-mol to 100 milli-mol, preferably 0.01 micro-mol to 10 milli-mol, per liter of the solvent. When the concentration of the organometallic complex of formula (1) is smaller than 0.001 micro-mol, a catalyst having a sufficiently high activity cannot be obtained. In contrast, when the concentration exceeds 100 milli-mol, the catalyst activity is not enhanced and the catalyst becomes costly.

As examples of the solvent used, there can be mentioned aliphatic hydrocarbons such as butane, pentane, hexane, heptane, octane, isooctane, nonane, decane, cyclopentane, cyclohexane, methylcyclohexane, cyclooctane and decaline; aromatic hydrocarbons such as benzene, toluene, xylene, ethylbenzene, cumene and trimethylbenzene; and halogenated hydrocarbons such as methylene chloride, chloroform, carbon tetrachloride, dichlorethane, chlorobenzene and dichlorobenzene. The reaction product obtained by trimerization of ethylene, namely, 1-hexene, can also be used as a solvent. These slvents may be used either alone or as a mixture of at least two thereof. To control the concentration of the organometallic complex of formula (1) in a reaction system for trimerization of ethylene, the solution of the organometallic complex in the solvent may be concentrated or diluted.

The contact of organometallic complex of formula (1) (i) with an alkylaminoalumoxane (ii) and other ingredients (iii), (iv) and/or (v) for the preparation of the catalyst is carried out usually at a temperature of −100 to 250° C., preferably 0 to 200° C. The contact time is not particularly limited, but is usually in the range of 1 minute to 24 hours, preferably 2 minutes to 2 hours. The operation for the contact of the above ingredients (i), (ii), (iii), (iv) and/or (v) is preferably carried out under conditions such that these ingredients are not in contact with air and moisture. The ingredients (i), (ii), (iii), (iv) and/or (v) used are preferably preliminarily dried.

In the step of preparing a catalyst by contacting the above ingredients (i), (ii), (iii), (iv) and/or (v) with each other, the partial pressure of ethylene in a reaction vessel is usually in the range of 0.00001 to 10,000 kg/cm$^2$, preferably 0.1 to 3,000 kg/cm$^2$ and more preferably 1 to 2,000 kg/cm$^2$.

The trimerization of ethylene according to the process of the present invention is carried out by contacting ethylene with the above-mentioned catalyst ingredients, namely, an organometallic complex of formula (1) (i), an alkylalumioxane (ii), and other ingredients (ii), (iv) and/or (v). The procedure for contacting ethylene with the catalyst ingredients is not particularly limited, and there can be mentioned, for example, a first procedure wherein (a) catalyst ingredients (i) and (ii); (b) catalyst ingredients (i), (ii) and (iii); (c) catalyst ingredients (i), (ii), (iii) and (iv); (d) catalyst ingredients (i), (ii) and (iv); (e) catalyst ingredients (i), (ii) and (v); or (f) catalyst ingredients (i), (ii), (v) and (iv), are contacted with each other in the presence of ethylene whereby reaction for trimerization of ethylene occurs simultaneously with the contact of catalyst ingredients; and a second procedure wherein (a) catalyst ingredients (I) and (ii); (b) catalyst ingredients (i), (ii) and (iv); (c) catalyst ingredients (i), (ii), (iii) and (iv); (d) catalyst ingredients (i), (ii) and (iv); (e) catalyst ingredients (i), (ii) and (v); or (f) catalyst ingredients (i), (ii), (v) and (iv), are preliminarily contacted with each other, and then, the respective catalyst ingredients are placed in contact with ethylene to effect trimerization of ethylene. In the first and second procedures, the order in which the respective catalyst ingredients are contacted with each other is not particularly limited.

The reaction temperature for trimerization of ethylene is usually in the range of −100 to 500° C., preferably 0 to 300° C. The reaction pressure is not particularly limited provided that the reaction is conducted in an ethylene atmosphere. Usually an absolute pressure of 0.01 to 3,000 kg/cm$^2$, preferably 0.1 to 2,000 kg/cm$^2$ is employed. The reaction time is usually in the range of 5 seconds to 6 hours.

The reaction can be conducted in a continuous manner wherein ethylene is continuously introduced so that the above-mentioned pressure is maintained, or in a batchwise manner wherein ethylene is preliminarily charged to a stated pressure, and then, the reaction is conducted, or a semi-batchwise manner. A raw material feed of ethylene may comprise a gas inert to the reaction such as nitrogen, argon or helium. The operation for the trimerization of ethylene is preferably carried out under conditions such that ethylene and the catalyst are not in contact with air and moisture. Preferably ethylene is preliminarily thoroughly dried.

To terminate the trimerization of ethylene, a deactivator such as water, an alcohol or an aqueous sodium hydroxide solution can be added to deactivate the catalyst. The deactivated catalyst can be removed by a known ash-removing procedure, for example, by extracting the catalyst with water or an aqueous alkali solution. The thus-produced 1-hexene is separated, for example, by a known extraction or distillation procedure. Side-reaction products such as polyethylene can be separated as a residue by a known centrifugal separation or by a known distillation of 1-hexene.

The invention will now be specifically described by the following examples that by no means limit the scope of the invention.

In the examples, determination of a chromium complex and products produced by trimerization of ethylene was conducted by the following methods.

(1) Determination of Organometallic Complex

An organometallic complex was analyzed according to infrared (IR) absorption spectroscopy using an infrared spectrophotometer "FTIR-8100" available from Shimadzu Corporation.

(2) Determination of Trimerization Products (i) Products having 4 to 8 carbon atoms contained in a reaction liquid were determined by gas chromatography using a gas chromatograph "GC-14A" available from Shimadzu Corporation equipped with a column "TC-1" available from GL Science Co. The analysis was carried out using a nitrogen carrier at an injection temperature of 280° C. and a detector temperature of 280° C. n-heptane was used as internal standard. The measurement was conducted while the column temperature was elevated from 40° C. to 250° C. after 1.2 μl of the reaction liquid was injected into the chromatograph.

(ii) Products having at least 10 carbon atoms contained in a reaction liquid were determined by gas chromatography using another gas chromatograph "GC-14A" available from Shimadzu Corporation equipped with a column "TC-1" available from GL Science Co. The analysis was carried out using a nitrogen carrier at an injection temperature of 300° C. and a detector temperature of 300° C. n-heptane was used as internal standard. The measurement was conducted while the column temperature was elevated from 50° C. to 300° C. after 1.4 μl of the reaction liquid was injected into the chromatograph.

(iii) Products contained in a gas atmosphere were determined by gas chromatography using a gas chromatograph "GC-9A" available from Shimadzu Corporation equipped with an $Al_2O_3$/KCl column available from Chrompack Co. The analysis was carried out using a nitrogen carrier at an injection temperature of 200° C., a detector temperature of 200° C. and a column temperature of 120° C. Absolute calibration curve was used. The measurement was conducted by injecting 0.2 ml of a collected gas into the chromatograph.

REFERENCE EXAMPLE 1

A Schlenk tube having an inner volume of 100 ml was charged with 126 mg of tris(3,5-dimethyl-1-pyrazolyl)methane having a tripod structure, which was synthesized by a method described in J. Amer. Chem. Soc., 92, 5118 (1970), 143 mg of tris(tetrahydrofuran)chromium trichloride (III) and 20 ml of tetrahydrofuran. The mixture was stirred for 12 hours in a nitrogen atmosphere. The thus-precipitated crystal was recovered by filtration to give tris(3,5-dimethyl-1-pyrazolyl)methanechromium trichloride (III) (IR [nujol]: 1565 $cm^{-1}$). This complex is hereinafter referred to as "complex A".

REFERENCE EXAMPLE 2

A Schlenk tube having an inner volume of 100 ml was charged with 346 mg of tris(3-phenyl-5-methyl-1-pyrazolyl)methane having a tripod structure, which was synthesized by a method described in J. Amer. Chem. Soc., 92, 5118 (1970), 255 mg of tris(tetrahydrofuran)chromium trichloride (III), 5 ml of tetrahydrofuran and 20 ml of toluene. The mixture was stirred at 95° C. for 24 hours in a nitrogen atmosphere. The thus-precipitated crystal was recovered by filtration to give tris(3-phenyl-5-methyl-1-pyrazolyl)methanechromium trichloride (III) (IR [KBr]: 1566 $cm^{-1}$). This complex is hereinafter referred to as "complex B".

REFERENCE EXAMPLE 3

A Schlenk tube having an inner volume of 100 ml was charged with 120 mg of tris(3-phenyl-1-pyrazolyl)methane having a tripod structure, which was synthesized by a method described in J. Amer. Chem. Soc., 92, 5118 (1970), 94 mg of tris(tetrahydrofuran)chromium trichloride (III) and 18 ml of toluene. The mixture was stirred at 100° C. for 12 hours in a nitrogen atmosphere. The thus-precipitated crystal was recovered by filtration to give tris(3-phenyl-1-pyrazolyl)methanechromium trichloride (III) (IR [KBr]: 1540 $cm^{-1}$). This complex is hereinafter referred to as "complex C".

REFERENCE EXAMPLE 4

A Schlenk tube having an inner volume of 100 ml was charged with 400 mg of tris(3-(4-tolyl)-1-pyrazolyl)methane having a tripod structure, which was synthesized by a method described in J. Amer. Chem. Soc., 92, 5118 (1970), 295 mg of tris(tetrahydrofuran)chromium trichloride (III) and 30 ml of toluene. The mixture was stirred at 100° C. for 12 hours in a nitrogen atmosphere. The thus-precipitated crystal was recovered by filtration to give tris(3-(4-tolyl)-1-pyrazolyl)methanechromium trichloride (III) (IR [KBr]: 1541 $cm^{-1}$). This complex is hereinafter referred to as "complex D".

COMPARATIVE EXAMPLE 1

A pressure-resistant stainless steel reactor having an inner volume of 300 ml, equipped with a thermometer and a stirring apparatus, was charged with complex A, prepared in Reference Example 1, and 60 ml of dry toluene in a nitrogen atmosphere, and the content was stirred. The rate of stirring was adjusted to 1,000 rpm. Then, a solution of tri-n-octylaluminum in toluene was introduced and the content was stirred for 30 minutes.

The reactor was heated to 80° C., and ethylene gas was introduced to an extent such that the pressure within the reactor reached 40 $kg/cm^2$ to initiate a trimerization reaction of ethylene. The reaction was continued for 30 minutes while the introduction of ethylene gas was continued so that the pressure of 40 $kg/cm^2$ was maintained during the reaction. Thereafter, water was injected by nitrogen into the reactor to deactivate the catalyst and terminate the reaction.

The reactor was cooled to room temperature and then the pressure was reduced to normal pressure. Products contained in the reaction liquid and the gas collected from the reactor were analyzed by gas chromatography. Results are shown in Table 1.

EXAMPLES 1 TO 3

A pressure-resistant stainless steel reactor having an inner volume of 300 ml, equipped with a thermometer and a stirring apparatus, was charged with a predetermined amount of complex A, prepared in Reference Example 1, 60 ml of dry toluene, and a predetermined amount of methylaluminoxane or a combination of methylaluminoxane with tri-n-octylaluminum in a nitrogen atmosphere. The content was stirred for 30 minutes.

The reactor was heated to 80° C., and the rate of stirring was adjusted to 1,000 rpm. Then, ethylene gas was introduced to an extent such that the pressure within the reactor reached 40 kg/cm$^2$ to initiate a trimerization reaction of ethylene. The reaction was continued for 30 minutes while the introduction of ethylene gas was continued so that the pressure of 40 kg/cm$^2$ was maintained during the reaction.

Thereafter, water was injected by nitrogen into the reactor to deactivate the catalyst and terminate the reaction.

The reactor was cooled to room temperature and then the pressure was reduced to normal pressure. Products contained in the reaction liquid and the gas collected from the reactor were analyzed by gas chromatography. Results are shown in Table 1.

EXAMPLES 4 TO 7

Ethylene gas was introduced into a pressure-resistant stainless steel reactor having an inner volume of 300 ml equipped with a thermometer and a stirring apparatus, so that the partial pressure of ethylene within the reactor reached 30 kg/cm$^2$, while being stirred. A predetermined amount of complex A or complex B, prepared in Reference Example 1 or Reference Example 2, 60 ml of dry toluene, and a predetermined amount of methylaluminoxane or a combination of methylaluminoxane with tri-n-octylaluminum or triisobutylaluminum were injected into the reactor by nitrogen. The content was stirred for 30 minutes.

The reactor was heated to 80° C., and the rate of stirring was adjusted to 1,000 rpm. Then, ethylene gas was introduced to an extent such that the partial pressure of ethylene reached 40 kg/cm$^2$ to initiate a trimerization reaction of ethylene. The reaction was continued for 30 minutes while the introduction of ethylene gas was continued so that the partial pressure of 40 kg/cm$^2$ was maintained during the reaction. Thereafter, water was injected by nitrogen into the reactor to deactivate the catalyst and terminate the reaction.

The reactor was cooled to room temperature and then the pressure was reduced to normal pressure. Products contained in the reaction liquid and the gas collected from the reactor were analyzed by gas chromatography. Results are shown in Table 1.

TABLE 1

| | | Examples | | | | | | | |
|---|---|---|---|---|---|---|---|---|---|
| | | C.1 | 1 | 2 | 3 | 4 | 5 | 6 | 7 |
| Catalyst ingredients: | | | | | | | | | |
| (1) Complx | | A | A | A | A | A | A | B | B |
| Amount μmol | [mg] | 3[1.4] | 3[1.4] | 3[1.4] | 3[1.4] | 3[1.4] | 3[1.4] | 3[1.9] | 3[1.9] |
| (2) Alkylaluminoxane *1 | | MAO | MAO | MAO | MAO | MAO | MAO | MAO | MAO |
| Conc. of soln. | (mmol/l) | — | 56 | 174 | 174 | 174 | 56 | 174 | 174 |
| Amount of soln. | (ml) | — | 9.8 | 6.2 | 3.2 | 6.2 | 9.8 | 6.2 | 2.1 |
| Al/Cr mol ratio | | — | 180 | 360 | 180 | 360 | 180 | 360 | 120 |
| (3) Alkyl-contg. compound *2 | | n-Oc$_3$Al | n-Oc$_3$Al | — | — | — | n-Oc$_3$Al | — | i-BU$_3$Al |
| Conc. of soln. | (mmol/l) | 334 | 334 | — | — | — | 334 | — | 174 |
| Amount of soln. | (ml) | 3.2 | 1.6 | — | — | — | 1.6 | — | 4.2 |
| Al/Cr mol ratio | | 360 | 180 | — | — | — | 180 | — | 240 |
| Reaction conditions: | | | | | | | | | |
| Ethylene pressure | (kg/cm$^2$) | 40 | 40 | 40 | 40 | 40 | 40 | 40 | 40 |
| Temperature | (° C.) | 80 | 80 | 80 | 80 | 80 | 80 | 80 | 80 |
| Time | (min) | 30 | 30 | 30 | 30 | 30 | 30 | 30 | 30 |
| Stirring rate | (rpm) | 1000 | 1000 | 1000 | 1000 | 1000 | 1000 | 1000 | 1000 |
| Results of trimerization: | | | | | | | | | |
| 1-hexene activity | (kg/g-Cr/h) | 11.4 | 20.7 | 24.5 | 18.5 | 33.5 | 29.9 | 40.1 | 33.1 |
| | (g/l-cata.soln./h) | 26.3 | 51.4 | 61.2 | 46.2 | 77.3 | 69.0 | 99.6 | 82.2 |
| Polymer/product | (wt. %) | <0.1 | 1.2 | 2.1 | 2.1 | <0.1 | 0.9 | 1.5 | 0.4 |
| Oligomer fraction C4 | (wt. %) | 0.1 | 0.3 | 0.3 | 0.2 | 0.3 | 0.3 | 0.1 | 0.4 |
| C6 | (wt. %) | 77.2 | 87.2 | 92.3 | 94.4 | 93.0 | 87.5 | 99.6 | 96.8 |
| C8≦ | (wt. %) | 22.7 | 12.5 | 7.4 | 5.4 | 6.7 | 12.2 | 0.3 | 2.8 |
| α-Purity *3 | (wt. %) | 99.8 | 99.9 | 99.9 | 99.9 | 99.8 | 99.9 | 99.5 | 99.2 |

Note:
*1 Alkylaluminoxane: MAO = Methylaluminoxane
*2 Alkyl group-containing compound: n-Oc$_3$Al = Tri-n-octylaluminum 1-Bu$_3$Al = Tri-isobutylaluminum
*3 α-Purity: 1-hexene fraction in C6 Oligomers

COMPARATIVE EXAMPLE 2

A pressure-resistant glass reactor having an inner volume of 150 ml, equipped with a thermometer and a stirring apparatus, was charged with complex A, prepared in Reference Example 1, and 60 ml of dry toluene in a nitrogen atmosphere, and the content was stirred. The rate of stirring was adjusted to 1,200 rpm. Then, a solution of methylaluminoxane in toluene was injected by nitrogen and the content was stirred for 30 minutes.

The reactor was heated to 80° C., and ethylene gas was introduced to an extent such that the pressure within the reactor reached 5 kg/cm² to initiate a trimerization reaction of ethylene, The reaction was continued for 30 minutes while the introduction of ethylene gas was continued so that the pressure of 5 kg/cm² was maintained during the reaction. Thereafter, water was injected by nitrogen into the reactor to deactivate the catalyst and terminate the reaction.

The reactor was cooled to room temperature and then the pressure was reduced to normal pressure. Products contained in the reaction liquid and the gas collected from the reactor were analyzed by gas chromatography. Results are shown in Table 2.

COMPARATIVE EXAMPLE 3

A pressure-resistant glass reactor having an inner volume of 150 ml, equipped with a thermometer and a stirring apparatus, was charged with complex A, prepared in Reference Example 1, and 60 ml of dry toluene in a nitrogen atmosphere, and the content was stirred. The rate of stirring was adjusted to 1,200 rpm. Then, a solution of triisobutylaluminum mixed with methylaluminoxane in toluene was injected by nitrogen and the content was stirred for 30 minutes.

The reactor was heated to 80° C., and ethylene gas was introduced to an extent such that the pressure within the reactor reached 5 kg/cm² to initiate a trimerization reaction of ethylene. The reaction was continued for 30 minutes while the introduction of ethylene gas was continued so that the pressure of 5 kg/cm² was maintained during the reaction. Thereafter, water was injected by nitrogen into the reactor to deactivate the catalyst and terminate the reaction.

The reactor was cooled to room temperature and then the pressure was reduced to normal pressure. Products contained in the reaction liquid and the gas collected from the reactor were analyzed by gas chromatography. Results are shown in Table 2.

EXAMPLES 8 TO 11

A pressure-resistant glass reactor having an inner volume of 150 ml, equipped with a thermometer and a stirring apparatus, was charged with a predetermined amount of an organometallic complex (complex B, complex C or complex D, prepared in Reference Examples 2 to 4, 60 ml of dry toluene, and a combination of an alkylaluminoxane and germanium tetrachloride, or a combination of alkylaluminoxane, an alkyl group-containing compound and germanium tetrachloride in a nitrogen atmosphere. The content was stirred at a stirring rate of 1,200 rpm for 30 minutes.

The reactor was heated to 80° C., and, while the rate of stirring was maintained at 1,200 rpm, ethylene gas was introduced to an extent such that the pressure within the reactor reached 5 kg/cm² to initiate a trimerization reaction of ethylene. The reaction was continued for 30 minutes while the introduction of ethylene gas was continued so that the pressure of 5 kg/cm² was maintained during the reaction. Thereafter, water was injected by nitrogen into the reactor to deactivate the catalyst and terminate the reaction.

The reactor was cooled to room temperature and then the pressure was reduced to normal pressure. Products contained in the reaction liquid and the gas collected from the reactor were analyzed by gas chromatography. Results are shown in Table 2.

TABLE 2

|  |  | Examples | | | | | |
|---|---|---|---|---|---|---|---|
|  |  | C.2 | C.3 | 8 | 9 | 10 | 11 |
| Catalyst ingredients: | | | | | | | |
| (1) Complx | | B | B | B | B | C | D |
| Amount μmol | [mg] | 16[10.3] | 16[10.3] | 16[10.3] | 16[10.3] | 16[10.3] | 16[10.3] |
| (2) Alkylaluminoxane *1 | | MAO | MAO | MAO | MAO | MAO | MAO |
| Conc. of soln. | (mmol/l) | 721 | 192 | 721 | 192 | 192 | 192 |
| Amount of soln. | (ml) | 8.0 | 5.0 | 8.0 | 5.0 | 5.0 | 5.0 |
| Al/Cr | mol ratio | 360 | 60 | 360 | 60 | 60 | 60 |
| (3) Alkyl-contg. compound *2 | | — | i-Bu₃Al | — | i-Bu₃Al | i-Bu₃Al | i-Bu₃Al |
| Conc. of soln. | (mmol/l) | — | 961 | — | 961 | 961 | 961 |
| Amount of soln. | (ml) | — | 5.0 | — | 5.0 | 5.0 | 5.0 |
| Al/Cr mol ratio | | — | 300 | — | 300 | 300 | 300 |
| (4) GeCl₄, Ge/Cr mol ratio | | — | — | 0.01 | 0.01 | 0.01 | 0.01 |
| Reaction conditions: | | | | | | | |
| Ethylene pressure | (kg/cm²) | 5 | 5 | 5 | 5 | 5 | 5 |
| Temperature | (° C.) | 80 | 80 | 80 | 80 | 80 | 80 |
| Time | (min) | 30 | 30 | 30 | 30 | 30 | 30 |
| Stirring rate | (rpm) | 1200 | 1200 | 1200 | 1200 | 1200 | 1200 |
| Results of trimerization: | | | | | | | |
| 1-hexene activity | (kg/g-Cr/h) | 2.9 | 3.7 | 3.6 | 4.6 | 5.7 | 5.1 |
|  | (g/l-cata.soln./h) | 30.5 | 39.0 | 38.0 | 47.6 | 60.2 | 53.8 |
| Polymer/product | (wt. %) | <0.1 | trace | trace | trace | trace | trace |
| Oligomer fraction C4 | (wt. %) | 2.6 | 9.4 | 0.3 | 4.7 | 3.5 | 2.1 |
| C6 | (wt. %) | 76.4 | 87.1 | 87.2 | 92.0 | 92.4 | 94.9 |
| C8≦ | (wt. %) | 21.0 | 3.5 | 12.5 | 3.3 | 4.1 | 3.0 |
| α-Purity *3 | (wt. %) | 95.6 | 94.3 | 95.0 | 94.8 | 95.5 | 95.1 |

Note:
*1 Alkylaluminoxane: MAO = Methylaluminoxane
*2 Alkyl group-containing compound: i-Bu₃Al = Tri-isobutylaluminum
*3 α-Purity: 1-hexene fraction in C6 oligomers

COMPARATIVE EXAMPLE 4 AND 5

A pressure-resistant stainless steel reactor having an inner volume of 300 ml, equipped with a thermometer and a stirring apparatus, was charged with a predetermined amount of complex A, prepared in Reference Example 1 and 60 ml of toluene in a nitrogen atmosphere, and the content was stirred. The rate of stirring was adjusted to 1,000 rpm. Then, a predetermined amount of methylaluminoxane or a combination of methylaluminoxane with tri-n-octylaluminum, and the mixture was stirred for 30 minutes.

The reactor was heated to 80° C., and then, ethylene gas was introduced to an extent such that the pressure within the reactor reached 40 kg/cm$^2$ to initiate a trimerization reaction of ethylene. The reaction was continued for 30 minutes while the introduction of ethylene gas was continued so that the pressure of 40 kg/cm$^2$ was maintained during the reaction. Thereafter, water was injected by nitrogen into the reactor to deactivate the catalyst and terminate the reaction.

The reactor was cooled to room temperature and then the pressure was reduced to normal pressure. Products contained in the reaction liquid and the gas collected from the reactor were analyzed by gas chromatography. Results are shown in Table 3.

EXAMPLES 12 TO 15

A pressure-resistant stainless steel reactor having an inner volume of 300 ml, equipped with a thermometer and a stirring apparatus, was charged in a nitrogen stream with a predetermined amount, of complex A or complex B, prepared in Reference Example 1 and 2, and N-phenylmaleimide and 60 ml of toluene in a nitrogen atmosphere. Then, a predetermined amount of methylaluminoxane, or a combination of methylaluminoxane with tri-n-octylaluminum, was added, and the mixture was stirred for 30 minutes.

The reactor was heated to 80° C. and the rate of stirring was adjusted to 1,000 rpm. Thereafter, ethylene gas was introduced to an extent such that the pressure within the reactor reached 40 kg/cm$^2$ to initiate a trimerization reaction of ethylene. The reaction was continued for 30 minutes while the introduction of ethylene gas was continued so that the pressure of 40 kg/cm$^2$ was maintained during the reaction. Thereafter, water was injected by nitrogen into the reactor to deactivate the catalyst and terminate the reaction.

The reactor was cooled to room temperature and then the pressure was reduced to normal pressure. Products contained in the reaction liquid and the gas collected from the reactor were analyzed by gas chromatography. Results are shown in Table 3.

TABLE 3

|  |  |  | Examples | | | | | |
|---|---|---|---|---|---|---|---|---|
|  |  |  | C.4 | C.5 | 12 | 13 | 14 | 15 |
| Catalyst ingredients: | | | | | | | | |
| (1) Complx |  |  | A | A | A | A | B | B |
|  | Amount μmol | [mg] | 3 | 3 | 3 | 3 | 3 | 3 |
| (2) Alkylaluminoxane *1 |  |  | MAO | MAO | MAO | MAO | MAO | MAO |
|  | Conc. of soln. | (mmol/l) | 56 | 174 | 56 | 174 | 174 | 56 |
|  | Amount of soln. | (ml) | 9.8 | 6.2 | 9.8 | 6.2 | 6.2 | 9.8 |
|  | Al/Cr mol ratio |  | 180 | 360 | 180 | 360 | 360 | 180 |
| (3) Alkyl-contg. compound *2 |  |  | n-Oc$_3$Al | — | n-Oc$_3$Al | — | — | i-BU$_3$Al |
|  | Conc. of soln. | (mmol/l) | 334 | — | 334 | — | — | 334 |
|  | Amount of soln. | (ml) | 1.6 | — | 1.6 | — | — | 1.6 |
|  | Al/Cr mol ratio |  | 180 | — | 180 | — | — | 180 |
| (4) N-phenylmaleimide, N/Cr mol ratio | | | — | — | 5 | 5 | 5 | 5 |
| Reaction Conditions: | | | | | | | | |
| Ethylene pressure |  | (kg/cm$^2$) | 40 | 40 | 40 | 40 | 40 | 40 |
| Temperature |  | (° C.) | 80 | 80 | 50 | 80 | 80 | 80 |
| Time |  | (min) | 30 | 30 | 30 | 30 | 30 | 30 |
| Stirring rate |  | (rpm) | 1000 | 1000 | 1000 | 1000 | 1000 | 1000 |
| Results of trimerization: | | | | | | | | |
| 1-hexene activity |  | (kg/g-Cr/h) | 20.7 | 24.5 | 28.2 | 27.5 | 33.2 | 32.1 |
|  |  | (g/l-cata.soln./h) | 51.4 | 61.2 | 70.0 | 68.2 | 82.4 | 79.7 |
| Polymer/product |  | (wt. %) | 1.2 | 2.1 | 1.7 | 2.0 | 0.1 | 0.1 |
| Oligomer fraction | C4 | (wt. %) | 0.3 | 0.3 | 0.3 | 0.4 | 0.1 | 0.1 |
|  | C6 | (wt. %) | 87.2 | 92.3 | 88.6 | 90.7 | 93.8 | 95.0 |
|  | C8≦ | (wt. %) | 12.5 | 7.4 | 11.1 | 8.9 | 6.1 | 4.9 |
| α-Purity *3 |  | (wt. %) | 99.9 | 99.9 | 99.9 | 99.9 | 99.9 | 99.9 |

Note:
*1 Alkylaluminoxane: MAO = Methylaluminoxane
*2 Alkyl group-containing compound: n-Oc$_3$Al = Tri-n-octylaluminum i-Bu$_3$Al = Tri-isobutylaluminum
*3 α-Purity: 1-hexene fraction in C6 oligomers The catalyst of the present invention, used for trimerization of ethylene, which comprises (i) a specific organometallic complex having a neutral multidentate ligand with a tripod structure, (ii) an aluminoxane, and at least one optional ingredient selected from (iii) a halogen-containing inorganic compound, (iv) an alkyl group-containing compound and (v) an amine compound and/or an amide compound, is stable and easy in handling. When the catalyst is used for trimerization of ethylene, 1-hexene can be produced with high efficiency and high selectivity with production of a minimized amount of polymers.

What is claimed is:

1. An organochromium complex, which is
tris(3-phenyl-5-methyl-1-pyrazolyl)methanechromium trichloride(III),
tris(3-phenyl-1-pyrazolyl)methanechromium trichloride (III), or
tris(3-(4-tolyl)-1-pyrazolyl)methanechromium trichloride (III).

2. The organochromium complex of claim 1, which is tris(3-phenyl-5-methyl-1-pyrazolyl)methanechromium trichloride(III).

3. The organochromium complex of claim 1, which is tris(3-phenyl-1-pyrazolyl)methanechromium trichloride (III).

4. The organochromium complex of claim 1, which is tris(3-(4-tolyl)-1-pyrazolyl)methanechromium trichloride (III).

5. A process for trimerizing ethylene, comprising trimerizing ethylene in the presence of a catalyst comprising at least one organochromium complex selected from the group consisting of:
tris(3-phenyl-5-methyl-1-pyrazolyl)methanechromium trichloride(III),
tris(3-phenyl-1-pyrazolyl)methanechromium trichloride (III), and
tris(3-(4-tolyl)-1-pyrazoly)methanechromium trichloride (III).

6. The process of claim 5, wherein the organochromium complex comprises tris(3-phenyl-5-methyl-1-pyrazolyl) methanechromium trichloride(III).

7. The process of claim 5, wherein the organochromium complex comprises tris(3-phenyl-1-pyrazolyl)methanechromium trichloride(III).

8. The process of claim 5, wherein the organochromium complex comprises tris(3-(4-tolyl)-1-pyrazolyl)methanechromium trichloride(III).

* * * * *